(12) United States Patent
Oh et al.

(10) Patent No.: US 11,039,392 B2
(45) Date of Patent: Jun. 15, 2021

(54) FREQUENCY-BASED WAKE-UP DEVICE AND SENSOR COMMUNICATION DEVICE USING SAME

(71) Applicant: UNIVERSITY OF ULSAN FOUNDATION FOR INDUSTRY COOPERATION, Ulsan (KR)

(72) Inventors: Hoon Oh, Ulsan (KR); Trang Tien Nguyen, Ulsan (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 114 days.

(21) Appl. No.: 16/465,610

(22) PCT Filed: Dec. 1, 2017

(86) PCT No.: PCT/KR2017/014043
§ 371 (c)(1),
(2) Date: Aug. 26, 2019

(87) PCT Pub. No.: WO2018/101803
PCT Pub. Date: Jun. 7, 2018

(65) Prior Publication Data
US 2020/0022080 A1 Jan. 16, 2020

(30) Foreign Application Priority Data

Dec. 1, 2016 (KR) .......................... 10-2016-0162903

(51) Int. Cl.
*H04W 52/02* (2009.01)
*G01S 5/00* (2006.01)

(52) U.S. Cl.
CPC ....... *H04W 52/0229* (2013.01); *G01S 5/0018* (2013.01); *H04W 52/0235* (2013.01); *A61B 2560/0219* (2013.01)

(58) Field of Classification Search
CPC .................... H04W 52/029; H04W 52/0235
(Continued)

(56) References Cited

U.S. PATENT DOCUMENTS

2017/0117756 A1* 4/2017 Muratov ................. H02J 7/025

FOREIGN PATENT DOCUMENTS

JP    2010050909 A    3/2010
JP    2012256959 A    12/2012
(Continued)

OTHER PUBLICATIONS

International Search Report issued in corresponding application No. PCT/KR2017/014043 dated Apr. 5, 2018 (5 pages).
(Continued)

*Primary Examiner* — Angel T Brockman
(74) *Attorney, Agent, or Firm* — Osha Bergman Watanabe & Burton LLP

(57) ABSTRACT

The present description relates to a frequency-based wake-up device and a sensor communication device using such the same. The present invention comprises: a RF signal to voltage converter for receiving a wireless signal including a first signal and a second signal and converting the frequency of the preamble to voltage to generate a driving voltage and provide the same; a decoder activated by the driving voltage and extracts ID information of the sensor communication device by decoding the second signal; and a signal processor that is activated by the driving voltage and compares the extracted ID information of the sensor communication device by the decoder with pre-stored ID information of a pre-determined sensor communication device and notifies of reception of a wake-up signal when the extracted ID information and the pre-stored ID information are the same.

11 Claims, 3 Drawing Sheets

(58) Field of Classification Search
USPC .......................................................... 370/311
See application file for complete search history.

(56) References Cited

FOREIGN PATENT DOCUMENTS

| | | | |
|---|---|---|---|
| KR | 20100068790 A | 6/2010 | |
| KR | 20100097107 A | 9/2010 | |
| KR | 20120068298 A | 6/2012 | |

OTHER PUBLICATIONS

Written Opinion of the International Searching Authority issued in corresponding application No. PCT/KR2017/014043 dated Apr. 5, 2018 (5 pages).

* cited by examiner

FREQUENCY-BASED WAKE-UP DEVICE AND SENSOR COMMUNICATION DEVICE USING SAME

TECHNICAL FIELD

The present disclosure relates to a frequency-based wake-up device, and more particularly to a frequency-based wake-up device capable of performing a remote activation operation of a sensor communication device in various forms without additional power consumption, and a sensor communication device using the device.

BACKGROUND ART

With a recent focus on the ubiquitous technology, the wireless sensor network (WSN) technology which is its foundation is gradually developing.

A wireless sensor network, which is also referred to as a Ubiquitous Sensor Network (USN), means a network composed of a sensor for sensing certain information, a processor for processing sensing information, and a plurality of small devices, that is, sensor communication devices, equipped with a wireless transceiver for transmitting the sensing information.

Such a sensor network is used for collecting information on the surrounding environment for various purposes such as military, logistics, medical care, and the like, unlike existing networks which are used as a means of communication.

For example, a sensor network may be disposed at a location where human access is not easy, to sense a temperature or humidity of a location, thereby solving the difficulty of manpower mobilization to report the environment status. Further, a sensor network enables regularly monitoring the status of patients even from the outside by installing a sensor communication device near the patient, just as u-Healthcare service. Therefore a sensor network is a technology which has a possibility of unlimited use.

Because of the characteristics that a wireless sensor network is wireless, batteries are generally used in a sensor communication device instead of being supplied power by a wire, thereby requiring a great deal of time and manpower to check the remaining batteries and replace the spent disposable batteries.

In order to solve such a problem, a method for effectively using a limited battery has been studied, and in recent years, a wake-up technique which selectively operates only some of sensor communication devices that requires sensing, and keep other nodes in a sleep mode which consumes minimum power, is being studied as one of such measures.

Korean Patent Publication No. 2009-0065152 and the like disclose a technology for activating a sensor communication device only when the wake-up device, which is equipped separately, receives a wake-up signal from an external device.

Even in such a case, the wake-up device has to keep operating in order to receive and analyze the wake-up signal, so there is a limitation that power is consumed by the wake-up device. Also, in another embodiment, the entire received a radio frequency RF signal is converted into digital to determine whether or not the signal is a wake-up signal. Therefore, the method consumes a large amount of power.

SUMMARY OF INVENTION

Technical Problem

The following description provides a frequency-based wake-up device capable of performing a remote activation operation of a sensor communication device in a variety of forms without consuming additional power, and a sensor communication device using such a wake-up device.

The features described herein may not be limited to the above-mentioned features, and other features not mentioned can be clearly understood by those skilled in the art from the following description.

In one general aspect, a frequency-based wake-up device includes a RF signal to voltage converter for receiving a wireless signal including a first signal and a second signal and performing a frequency-voltage conversion of the preamble to generate and provide a driving voltage, a decoder decoding the second signal to extract ID information of a sensor communication device, and a signal processor which is activated by the driving voltage and compares the extracted the ID information of the sensor communication device from the decoder with pre-stored ID information of a pre-determined sensor communication device and notifies of reception of a wake-up signal when the extracted ID information and the pre-stored ID information are the same.

The wireless signal is an RF signal. The wake-up signal is a digital signal and includes the preamble as a preamble area, and a data area into which the second signal is converted.

The RF signal to voltage converter converts the preamble of the received RF-signal to generate the driving voltage.

The preamble has a length that varies depending on the level of the driving voltage.

The wireless signal further includes a third signal. The wake-up signal which is converted from the third signal further includes a wake-up mode area containing wake-up mode information of the sensor communication device. The decoder decodes the third signal to extract the wake-up mode information when the wireless signal is the wake-up signal.

The signal processor determines the sensor communication device to enter a wake-up mode based on the wake-up mode information.

The signal processor compares the extracted ID information of the sensor communication device from the decoder with the pre-stored ID information of a pre-determined sensor communication device, and transmits the wireless signal that is identical to the wireless signal to another sensor communication device when the ID information are not identical to each other.

When a wireless signal which is identical to the wireless signal is transmitted to another sensor communication device, the RF signal to voltage converter converts the frequency of the preamble to voltage to generate a driving voltage, and the preamble has a length that varies according to the level of the driving voltage.

The RF signal to voltage converter includes a signal pre-processor for band-pass filtering and removing noise of the wireless signal based on a transmission frequency band of the wireless signal; rectifier for rectifying the output of the signal pre-processor; a smoothing module for smoothing the output of the rectifier to generate DC voltage; and voltage regulator for regulating and outputting DC voltage which is output from the smoothing module.

In another general aspect, a sensor communication device includes an antenna for receiving a wireless signal including a first signal and a second signal; a sensor driving module for collecting and providing sensing information through a sensor, and actively varying an operation mode according to the frequency of use of the sensor, and a wake-up device which performs frequency-converting of the preamble to generate a self-driving voltage, extracts ID information of the sensor communication device from the second signal, compares with pre-stored ID information of a pre-determined sensor communication device, and sets forcibly an operation mode to a normal mode when the extracted ID information is same with the pre-stored ID information.

The wireless signal further includes a third signal. The wake-up device extracts wake-up mode information from the third signal and controlling the operation mode of the sensor driving module subdivided by the extracted wake-up mode information.

The wake-up device extracts the ID information of the sensor communication device from the second signal, compares the extracted ID information with a pre-stored ID information and transmits an identical as the wireless signal to another sensor communication device.

Effects of Invention

A frequency-based wake-up device and a sensor communication device using such the wake-up device according to the following description generates self-generated power by converting a first signal in a wireless signal to voltage, thereby minimizing power consumption.

Further, by selectively decoding only a second signal corresponding to the ID information of the sensor communication device, not the entire wireless signal, power consumption is reduced compared with a conventional method.

The following description relates to the wake-up device which in addition to simply determining whether or not to activate the sensor communication device by a wake-up signal, also controls in detail the activation state of the sensor communication device, by receiving and analyzing the wake-up signal which includes wake-up mode information.

Other features and aspects will be apparent from the following detailed description, the drawings, and the claims.

METHOD FOR CARRYING OUT THE INVENTION

Figure 1:
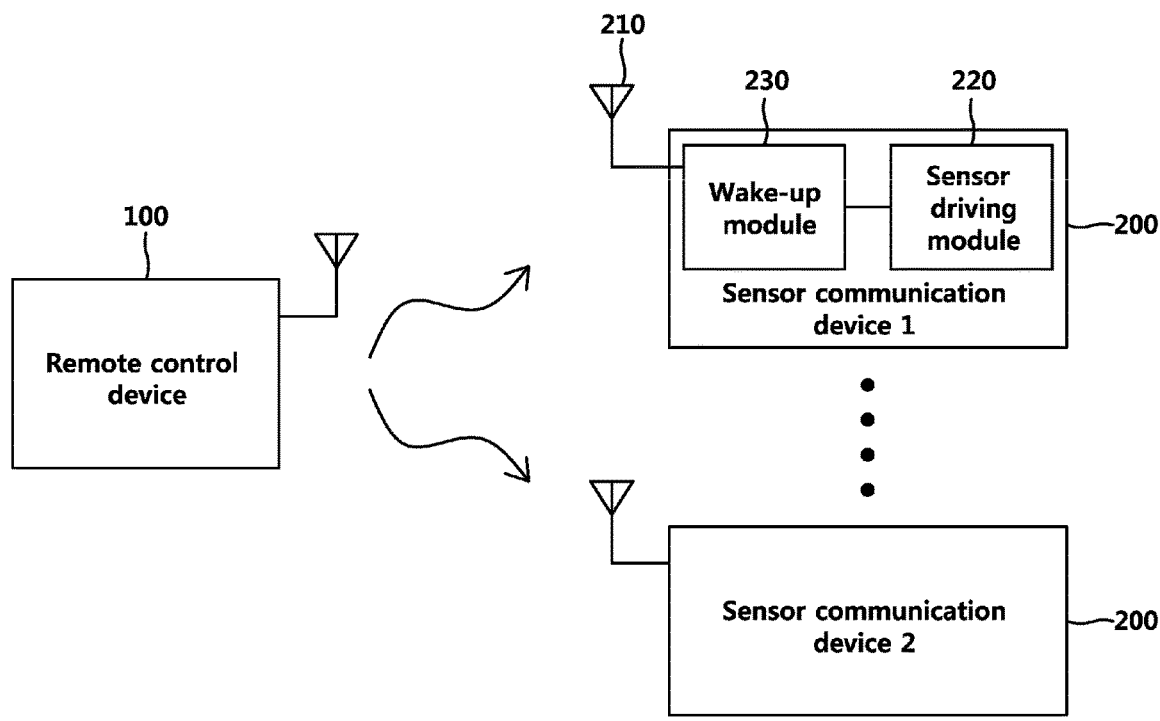
FIG. 1 is a diagram illustrating a sensor network according to an example.

The technical terms used in the present description are used only to describe specific embodiments and are not intended to limit the present description. In addition, the technical terms used in the present description should be construed in a sense generally understood by a person having ordinary skill in the art to which the present description belongs, unless otherwise defined in the present description, should not be construed to mean, or be interpreted in an excessively reduced sense. In addition, when a technical term used in the present description is an erroneous technical term that does not accurately express the concept of the present description, it should be understood with a replaced technical term that can be understood by a person having ordinary skill in the art. In addition, the general terms used in the present description should be interpreted according to a predefined or prior context, and should not be construed in an excessively reduced sense.

The singular expressions used in the present description include plural expressions as well unless the context clearly indicates otherwise. The terms "comprises" or "includes" and the like should not be construed as encompassing various elements or various operations and some elements or operations may not be included, or may further include additional elements or operations.

Hereinafter, embodiments of the present description will be described in detail with reference to the accompanying drawings, wherein reference numerals refer to the same or similar elements throughout the drawings and a duplicate description thereof will be omitted.

Descriptions of features that are known in the art may be omitted for increased clarity and conciseness. The drawings are provided to assist the reader in gaining a comprehensive understanding, and are not to be construed as being limited to the examples described herein.

FIG. 1 is a diagram illustrating a sensor network according to an example.

Referring to FIG. 1, the sensor network of the following description includes a remote control device 100 and at least one sensor communication device 200. Each of the sensor communication devices 200 has an antenna 210 for transmitting and receiving a wireless signal, a sensor driving module 220 for collecting and providing sensing information and actively varies the operation mode according to the frequency of use of the sensor, and a wake-up device 230 for receiving and analyzing a wake-up signal provided by the remote controller 100 and forcibly sets the operation mode of the sensor driving module 220 to normal mode according to the analysis result.

In the following description, each of the sensor communication devices 200 has the wake-up device 230 which forcibly turns off the sleep mode of the sensor communication device 200 by responding to the wake-up signal provided by the remote control device 100, thereby the sleep mode of each of the sensor communication devices 200 may be released by an external device which is the remote control device 100.

In particular, the wake-up device 230 of the following description self-generates the wake-up device drive power by the wireless signal, thereby preventing the waste of power by the wake-up device 230.

Figure 2:
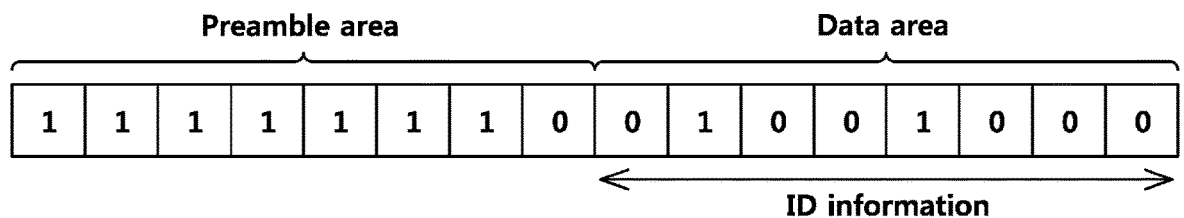
FIG. 2 is a diagram showing a wake-up signal according to an example.

FIG. 2 is a diagram illustrating a wake-up signal according to an example. The wireless signal is an RF signal, that is, an analog signal and further divided into a first signal and a second signal. As shown in the example of FIG. 2, the wake-up signal, as a digital signal, has a preamble area, which is the preamble, and a data area into which the second signal is converted. In the example of FIG. 2, the preamble area is shown in digital format, but it is merely to show that the wake-up signal is a digital signal, and in reality, only the second part is decoded and converted into digital format, and the preamble area is used for generating a driving voltage of the wake-up device at RF signal stage. In the data area, ID information of the sensor communication device to be activated is stored.

In the following description, the frequency of the preamble is converted into voltage to generate a wake-up device drive power, and the magnitude and length of the preamble for the wake-up device are adjustable according to the magnitude of the wake-up device drive power.

Figure 3:
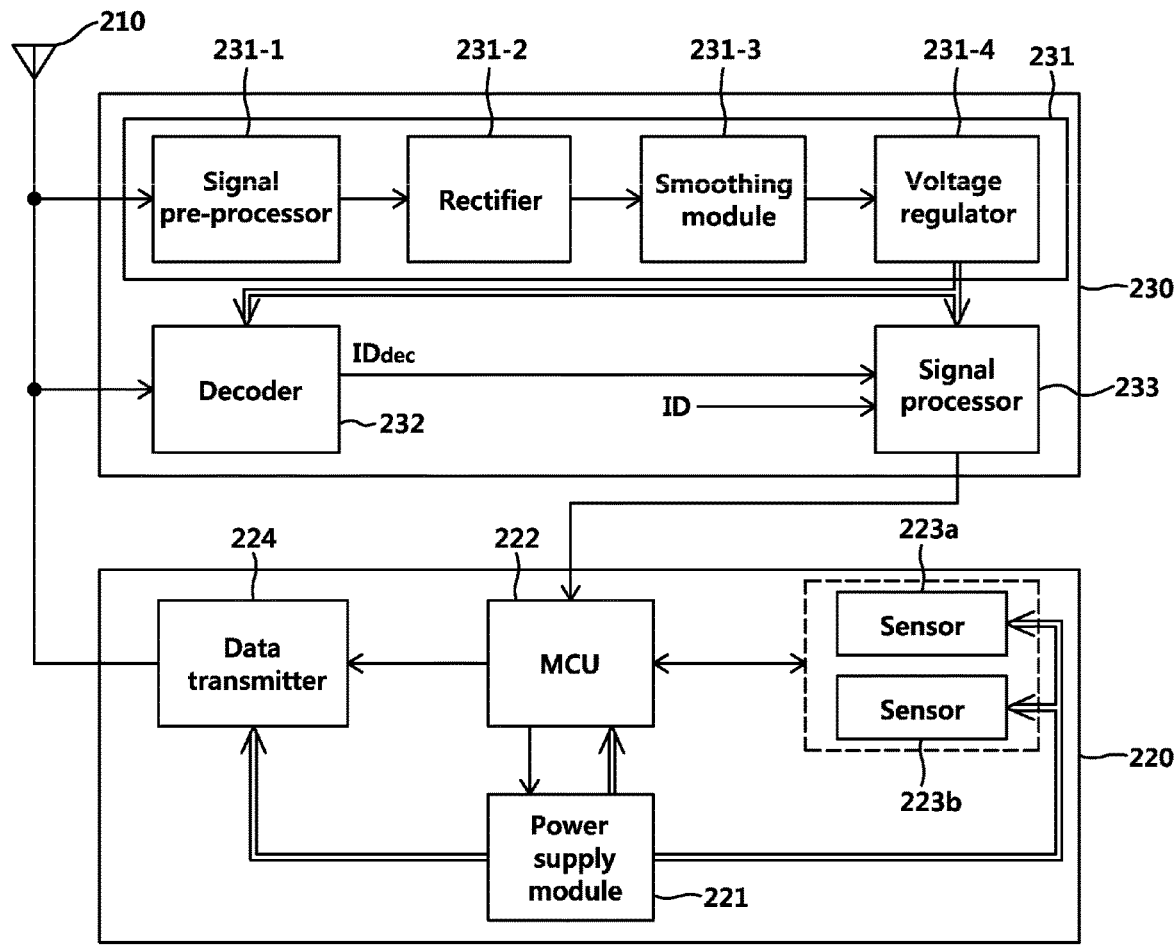
FIG. 3 is a diagram illustrating a detailed configuration of a wake-up device according to an example.

FIG. 3 is a diagram illustrating a detailed configuration of a wake-up device according to an example.

Referring to FIG. 3, the wake-up device 230 of the present example may include a RF signal to voltage converter 231, a decoder 232, and a signal processor 233.

The RF signal to voltage converter 231 performs a frequency-voltage conversion based on the preamble of the wireless signal received by the antenna 210, thereby generating DC voltage for driving the wake-up device.

The RF signal to voltage converter 231 of the present example may include a signal pre-processor 231-1, a rectifier 231-2, a smoothing module 231-3, voltage regulator 231-4, and the like. The signal pre-processor 231-1 performs band pass filtering on various wireless signals received by the antenna 210 so that only the wireless signal having a transmission frequency band of a wake-up signal is selectively output. Harmonic noise included in the band-pass filtered wireless signal is removed by noise removal function.

The rectifier 231-2 rectifies a signal which is output from the signal pre-processor 231-1 and the smoothing module 231-3 removes AC voltage remaining in the output signal of the rectifier 231-2 so that only the smoothed DC component may be output.

The voltage regulator 231-4 regulates DC voltage from the smoothing module 231-3 to output DC voltage having a constant voltage value regardless of external conditions.

The decoder 232 is activated by the DC voltage provided by the RF signal to voltage converter 231, and decodes the second signal of the wireless signal to extract the ID information $ID_{dec}$.

The signal processor 233 also is activated by the DC voltage provided by the RF signal to voltage converter 231. The signal processor 233 stores and manages the ID information ID of the sensor communication device allotted to the wake-up device 230. The signal processor 233 compares the ID information $ID_{dec}$ of the sensor communication device extracted by the decoder 232 with previously stored ID information ID and request the activation of the sensor communication device 200 only when the pieces of information are identical to each other.

The sensor driving module 220 (particularly, MCU 222), which is operating in a sleep mode, controls the power supply module 221 to supply drive power to MCU 222, the sensors 223a and 223b, and the data transmitter 224 for operation activation. Necessary information is collected by the sensors 223a and 223b, and then transmitted by the antenna via the data transmitter 224. That is, the sleep mode of the sensor driving module 220 is released and the sensor driving module 220 operates normally.

According to another example, the ID information $ID_{dec}$ of the sensor communication device extracted by the decoder 232 is compared with previously stored sensor communication device ID information (ID), and in the case the pieces of ID information are not identical to each other, the received wireless signal may be transmitted to another sensor communication device. Because the preamble of the wireless signal is used for the operation of the decoder 232 and the transmission of the wireless signal to another sensor communication device, a signal that will act as a wake-up signal in another sensor communication device cannot be generated with the ID information obtained from the second signal only. Therefore, the signal processor 233 generates a wireless signal using previously stored information corresponding to the preamble area and the ID information $ID_{dec}$ obtained from the wireless signal and transmits the same. The transmitted wireless signal is substantially identical to the received wireless signal. In an example of the method of operation, as FIG. 3 illustrates, the sensor driving module 220 may be activated to perform the operation because the data transmitter 224 is disposed in the sensor communication device. In this case, the sensors 223a and 223b are not operating. In addition, the data transmitter 224 may not be disposed in the wake-up device 230 nor in the sensor driving module 220 but may be included as a separate configuration. However, the positional change of the configuration for transmitting and receiving data is merely a design change for those of ordinary skill in the art. In this regard, the forwarding operation method may have two cases, when the sleep mode of the sensor driving module 220 is released and when the sleep mode is not released. Hereinafter, the effect of the forwarding operation will be described in more detail. When the ID of the sensor communication device extracted by the decoder 232 differs from previously stored sensor communication device ID, thus the wireless signal is transmitted to another sensor communication device, that is, when forwarded, the wireless signal may wake the sensor communication device up which is disposed apart where the direct communication was not available. When a wireless signal is transmitted to a sensor communication device y which is operating close to a certain sensor communication device x to wake up, the sensor communication device y transmits a wireless signal to x, which is another sensor communication device in the method explained above, thereby waking up the sensor communication device x which is disposed far away. Information about a destination or another sensor communication device may be included in a separate area in a wake-up signal or may be implemented by being forwarded to another sensor communication device which is connected according to a predetermined command.

In the present description, MCU 222 receives minimum power, that is, standby power from the power supply module 221 even when the sensor driving module 220 is in the sleep mode. Because if MCU 222 is completely powered off, all internal data (e.g., time sync information, state information, etc.) of MCU is deleted that MCU 222 may not be able to perform a continuous collecting of sensor information. That is, the present description minimizes power consumption but ensures continuous operation of the sensor module.

In addition, in the present description, the wireless signal may further include a third signal, and the wake-up signal to which the third signal is converted may further include a wake-up operation mode area for storing wake-up operation mode information. In this case the wake-up device may also vary the wake-up mode of the sensor communication device 200 based on the wake up operation mode information.

That is, further to simply determining the activation of the sensor communications device by the wake-up signal, the wake-up device may control in detail the operation of the sensor communication section 200 is activated in which state.

For example, when there is a plurality of sensors disposed in the sensor communication device, a plurality of sensors are classified into a plurality of groups. And then a sensor group to be activated per wake-up mode is controlled, or the operation cycle of the sensor group is controlled per sensor group, or activated sensor group and the operation cycle of the sensor are may be controlled together.

Figure 4:
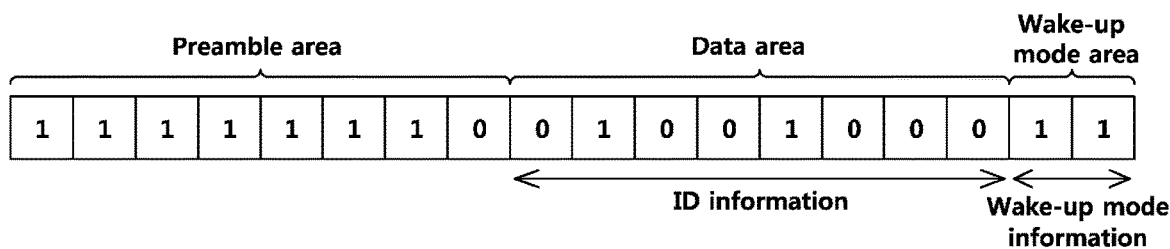
FIG. 4 is a diagram showing a wake-up signal according to another example.

FIG. 4 is a diagram illustrating a wake-up signal according to another example. According to another example, when a wireless signal further includes a third signal, a wake-up signal additionally includes a wake-up mode area corresponding thereto. Referring to FIG. 4, the data area of the wake-up signal includes ID information of the sensor communication device to be activated and the wake-up mode information is stored in the wake-up mode area.

Figure 5:
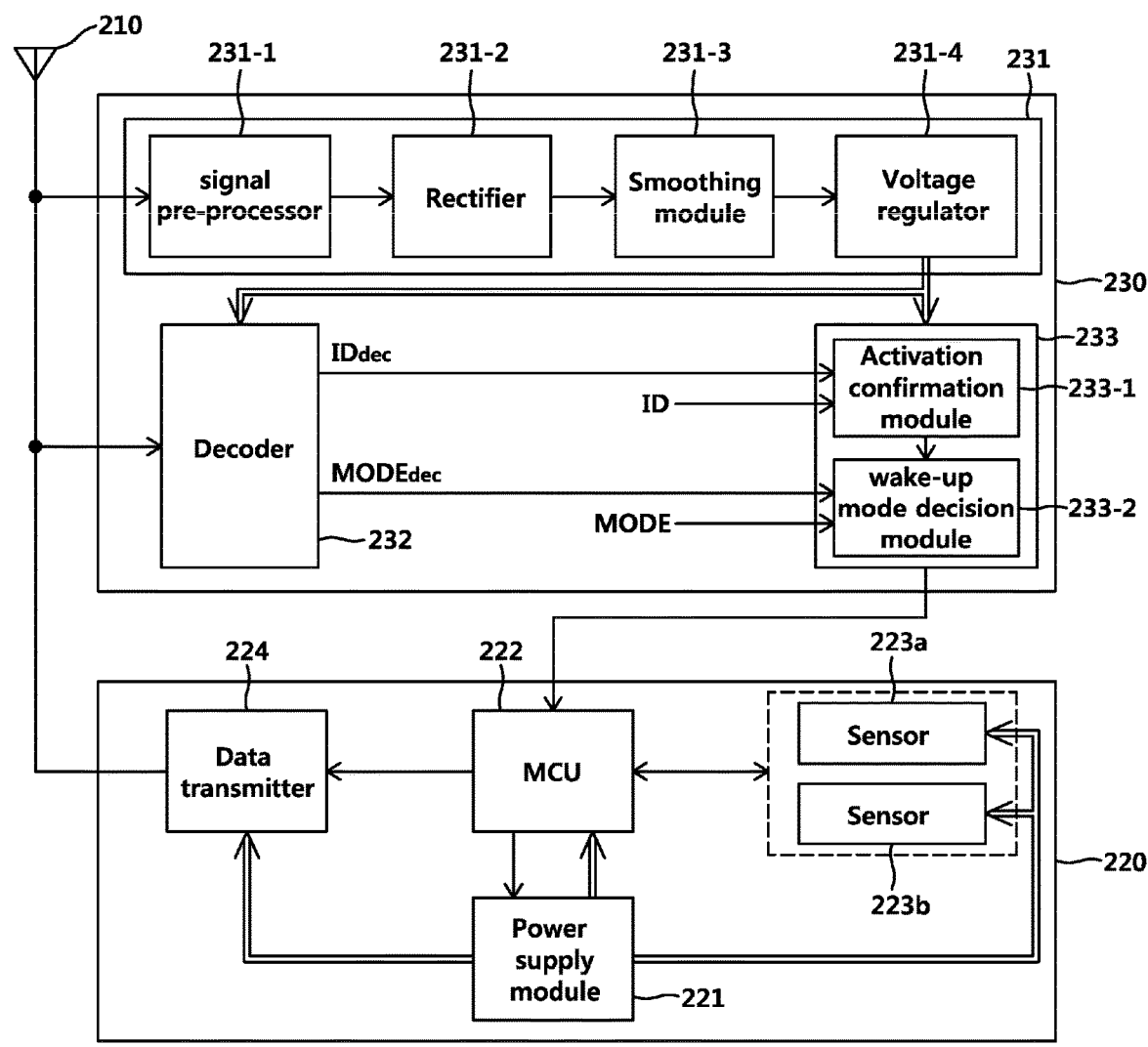
FIG. 5 is a diagram illustrating a detailed configuration of a wake-up device according to another example.

FIG. 5 illustrates a detailed configuration of a wake-up device according to another example. This is a wake-up device for receiving and analyzing the wake-up signal including ID information and wake-up mode information of FIG. 4.

As illustrated in FIG. 5, the decoder 232 disposed in the wake-up device 230 according to another example decodes the second signal and the third signal of the wireless signal so that the decoder 232 extracts ID information and the wake-up mode information.

The signal processor 233 further includes an activation confirmation module 233-1 and a wake-up mode decision module 233-2. Therefore, the signal processor 233 may control the operation state of the sensor communication device 200 in detail, in addition to simply determining whether or not to activate the sensor communication device.

The activation confirmation module 233-1 stores and manages ID information ID allotted to a sensor communication device, compares the ID information $ID_{dec}$ of the sensor communication device extracted by the decoder 232, and activates operation of the wake-up mode decision module 233-2 only when the pieces of ID information are identical to each other. The wake-up mode decision module 233-2 stores and manages wake-up mode information MODE which may be supported by the sensor communication device, and the mode information $MODE_{dec}$ extracted by the decoder 232 is compared and analyzed thereby determining and notifying the wake-up mode of the sensor communication device based on the wake-up mode information. For example, if the wake-up mode information $MODE_{dec}$ extracted by decoder 232 is n (n is a natural number) bits, the number of wake-up mode which can be supported the sensor communication device may be $2^n$, and the wake-up mode decision module 233-2 may output a total of $2^n$ control values according to the value of the extracted wake-up mode information $MODE_{dec}$. Then, the sensor communication device may further subdivide its operation mode into $2^n$ modes, and may variously control the operation and the operation period of each sensor according to the subdivided operation mode.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation.

Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A frequency-based wake-up device comprising:
   a RF signal to voltage converter for receiving a wireless signal including a first signal, a second signal, and a third signal and for performing a frequency-voltage conversion of a preamble of the wireless signal to generate and provide a driving voltage;
   a decoder which is activated by the driving voltage, decodes the second signal to extract ID information of a sensor communication device; and
   a signal processor which is activated by the driving voltage and compares the extracted ID information of the sensor communication device from the decoder with pre-stored ID information of a pre-determined sensor communication device and notifies of reception of a wake-up signal when the extracted ID information and the pre-stored ID information are the same, wherein
   the wake-up signal is a digital signal and includes a preamble area as the preamble and a data area to which the second signal is converted,
   the wake-up signal is converted from the third signal and further includes a wake-up mode area containing wake-up mode information of the sensor communication device, and
   the decoder decodes the third signal to further extract the wake-up mode information when the wireless signal is the wake-up signal.

2. The frequency-based wake-up device of claim 1, wherein the wireless signal is a radio frequency signal.

3. The frequency-based wake-up device of claim 2, wherein the RF signal to voltage converter converts a frequency of the preamble to generate the driving voltage.

4. The frequency-based wake-up device of claim 3, wherein the preamble has a length that varies according to the level of the driving voltage.

5. The frequency-based wake-up device of claim 1, wherein the signal processor determines the sensor communication device to enter a wake-up mode based on the wake-up mode information.

6. The frequency-based wake-up device of claim 1, wherein the signal processor compares the extracted ID information of the sensor communication device from the decoder with the pre-stored ID information of a pre-determined sensor communication device, and transmits the wireless signal that is identical to the wireless signal to another sensor communication device when the ID information are not identical to each other.

7. The frequency-based wake-up device of claim 6, wherein the RF signal to voltage converter converts a frequency of the preamble to voltage for generating the driving voltage, and
   wherein the preamble has a length which varies according to the level of the driving voltage.

8. The frequency-based wake-up device of claim 1 wherein the RF signal to voltage converter includes:
   a signal pre-processor for performing band-pass filtering and removing noise of the wireless signal based on a transmission frequency band of the wireless signal;
   a rectifier for rectifying the output of the signal pre-processor;
   a smoothing module for smoothing the output of the rectifier to generate DC voltage; and
   a voltage regulator for regulating and outputting the DC voltage which is output from the smoothing module.

9. A sensor communication device comprising:
an antenna for receiving a wireless signal including a first signal, a second signal, and a third signal, wherein the third signal is a wakeup mode information of the sensor communication device;
a sensor driving module for collecting and providing sensing information by a sensor, and actively varying an operation mode according to the frequency of use of the sensor; and
a wake-up device which performs frequency-converting of a preamble of the wireless signal to generate a self-driving voltage, extracts ID information of the sensor communication device from the second signal, compares with pre-stored ID information of a pre-determined sensor communication device, and sets forcibly an operation mode to a normal mode when the extracted ID information is same with the pre-stored ID information, wherein
a wake-up signal is converted from the third signal and includes a wake-up mode area containing the wake-up mode information,
the wake-up signal is a digital signal and includes a preamble area as the preamble and a data area to which the second signal is converted, and
the wake-up device decodes the third signal to further extract the wake-up mode information when the wireless signal is the wake-up signal.

10. The sensor communication device of claim 9, wherein the wake-up device extracts the wake-up mode information from the third signal and controls the operation mode of the sensor driving module subdivided by the extracted wake-up mode information.

11. The sensor communication device of claim 9, wherein the wake-up device extracts ID information of the sensor communication device from the second signal, comparing the extracted ID information with a pre-stored ID information, and transmits an identical signal as the wireless signal to another sensor communication device.

* * * * *